US008232395B2

(12) United States Patent
Graeser et al.

(10) Patent No.: US 8,232,395 B2
(45) Date of Patent: Jul. 31, 2012

(54) METHOD FOR PRODUCING 2-(2-AMINOPYRIMIDIN-4-YL)-1H-INDOLE-5-CARBOXYLIC ACID DERIVATIVES

(75) Inventors: Joachim Graeser, Frankfurt am Main (DE); Guenter Billen, Frankfurt am Main (DE); Adolf Linkies, Frankfurt am Main (DE); Tobias Metzenthin, Frankfurt am Main (DE)

(73) Assignee: Sanofi, Paris (FR)

( * ) Notice: Subject to any disclaimer, the term of this patent is extended or adjusted under 35 U.S.C. 154(b) by 1105 days.

(21) Appl. No.: 11/949,294

(22) Filed: Dec. 3, 2007

(65) Prior Publication Data

US 2008/0214813 A1 Sep. 4, 2008

Related U.S. Application Data

(63) Continuation of application No. PCT/EP2006/004645, filed on May 17, 2006.

(30) Foreign Application Priority Data

Jun. 1, 2005 (DE) .................. 10 2005 025 225

(51) Int. Cl.
*C07D 403/04* (2006.01)
(52) U.S. Cl. .................................. 544/331
(58) Field of Classification Search .................. 544/331
See application file for complete search history.

(56) References Cited

U.S. PATENT DOCUMENTS

| 7,285,560 B2 | 10/2007 | Ritzeler et al. | |
|---|---|---|---|
| 2003/0119820 A1 | 6/2003 | Ritzeler et al. | |
| 2004/0116494 A1* | 6/2004 | Michaelis et al. | 514/394 |
| 2007/0244139 A1 | 10/2007 | Ritzeler | |

FOREIGN PATENT DOCUMENTS

| WO | WO 01/30774 A1 | 5/2001 |
|---|---|---|
| WO | WO 2004/022553 A1 | 3/2004 |
| WO | WO 2004/089913 | * 10/2004 |

OTHER PUBLICATIONS

Hirao, K., et al., Rhodium-Catalyzed Carbonylation of 2-Alkynylaniline: Syntheses of 1,3-Dihydroindol-2-ones, Tetrahedron Letters, (1995) vol. 36, No. 35. pp. 6243-6246.
Jiang, B., et al., Synthesis of Indolylpyrimidines via Cross-Coupling of Indolylboronic Acid with Chloropyrimidines: Facile Synthesis of Meridianin D, Heterocycles, vol. 53, No. 7, 2000.
Beletskaya I.P. et al., "The Nickel-Catalyzed Sonogashira-Hagihara Reaction", *Tetrahedron Letters* 44:5011-5013 (2003).
Vazquez E. et al., "A Non-Cryogenic Method for the Preparation of 2-(Indolyl) Borates, Silanes and Silanols", *J Org. Chem.* 67(21):7551-7552 (2002).

* cited by examiner

*Primary Examiner* — Deepak Rao
(74) *Attorney, Agent, or Firm* — Scully, Scott, Murphy & Presser, P.C.; Robert Kajubi; Kelly L. Bender

(57) ABSTRACT

This invention relates to a novel process for obtaining a compound of formula I:

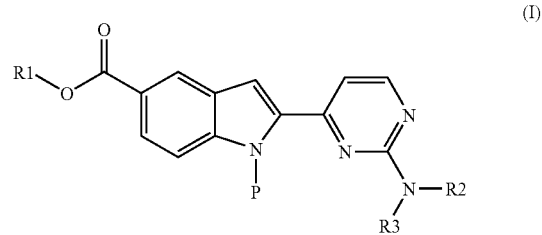

wherein the values of R1, R2, and R3 and P are as described in the specification.

16 Claims, No Drawings

METHOD FOR PRODUCING 2-(2-AMINOPYRIMIDIN-4-YL)-1H-INDOLE-5-CARBOXYLIC ACID DERIVATIVES

BACKGROUND OF THE INVENTION

It is known that indole derivatives are used as units for the synthesis of active pharmaceutical ingredients. For example, 2-(2-aminopyrimidin-4-yl)-1H-indole-5-carboxylic acids or their salts are important units for the preparation of IkB kinase inhibitors (see WO 01/30774 A1):

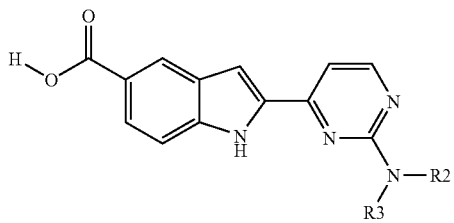

2-(2-Aminopyrimidin-4-yl)-1H-indole-5-carboxylic acids can be prepared by classical Fischer indole synthesis starting from the corresponding 4-acetylpyrimidines (III) and 4-hydrazinobenzoic acid (II) (see scheme 1):

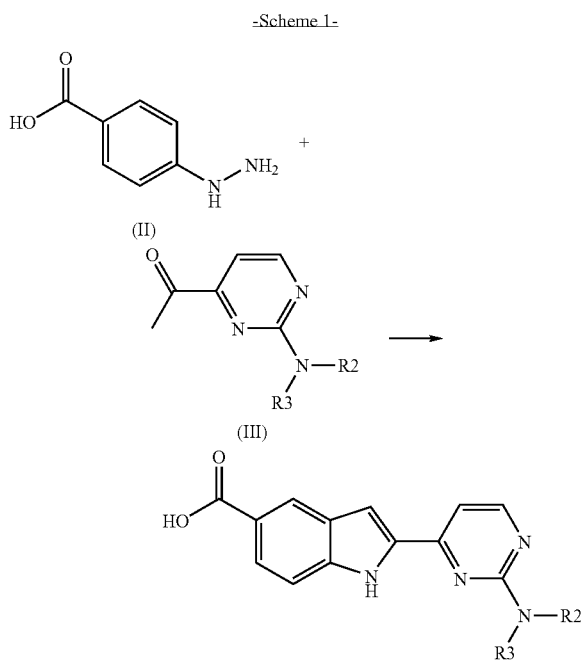

One disadvantage here is the severe reaction conditions which are required for a full conversion. Secondly, the products of this reaction are obtained in a mixture with the corresponding oligomers, which leads to a poor isolability, especially with regard to the filtration times. Moreover, these oligomers, owing to the low solubility of 2-(2-aminopyrimidin-4-yl)-1H-indole-5-carboxylic acids in organic solvents, can only be removed with difficulty and are entrained as an impurity in the further reactions, in some cases up to the active ingredient.

SUMMARY OF THE INVENTION

The invention relates to a process for preparing compounds of the formula I and to novel intermediates in obtaining the compound of the formula I. The indole derivatives mentioned are suitable intermediates for preparing Ikb kinase inhibitors (WO 01/30774 A1; WO2004/022553).

DETAILED DESCRIPTION OF THE INVENTION

It is an object of the present invention to find an industrial process for preparing the compounds of the formula I which does not have the disadvantages mentioned.

A process has now been found for obtaining the compound of the formula I

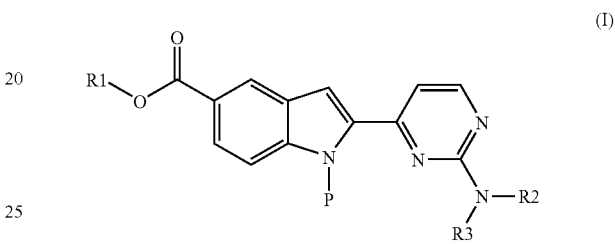

where
R1 is
1) a hydrogen atom,
2) —($C_1$-$C_{12}$)-alkyl,
3) —($C_6$-$C_{14}$)-aryl,
4) —($C_3$-$C_8$)-cycloalkyl or
5) a 4- to 15-membered Het ring,
R2 and R3 are the same or different and are each independently
1) a hydrogen atom,
2) ($C_1$-$C_{12}$)-alkyl,
3) —($C_6$-$C_{14}$)-aryl where aryl is unsubstituted or mono-, di- or trisubstituted by —($C_{1-6}$)-alkyl,
4) —($C_3$-$C_8$)-cycloalkyl or
5) a 4- to 15-membered Het ring,
P is a hydrogen atom or a nitrogen protecting group,
which comprises
a) reacting a boronoindole of the formula IV

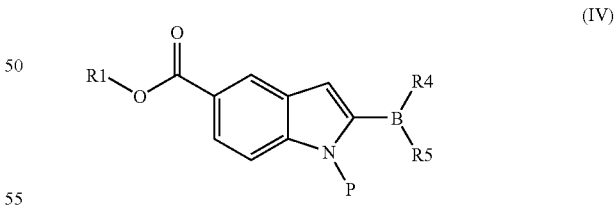

in which R1 is as defined in formula I,
R4 and R5 are the same or different and are each independently
1) —OH,
2) —O—($C_1$-$C_{12}$)-alkyl,
3) —O—($C_6$-$C_{14}$)-aryl,
4) —O—($C_{3-8}$)-cycloalkyl,
5) —($C_1$-$C_{12}$)-alkyl or
6) —O-Het, where Het is a 4- to 15-membered Het ring, or
R4 and R5, together with the boron atom to which they are bonded, form a ring having 4, 5, 6 or 7 carbon atoms in the ring and the ring may, instead of the particular carbon atoms, contain two oxygen atoms or two oxygen atoms and one nitrogen atom, P is a hydrogen atom or a nitrogen protecting group, with an aminopyrimidine of the formula V

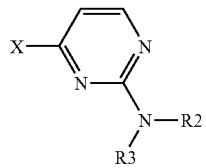

(V)

in which R2 and R3 are each as defined in formula I and

X is 1) halogen,
2) —O—SO$_2$—R2 or
3) —O—C(O)—R2, and detaching any nitrogen protecting group present, or b) reacting a boronoindole of the formula IV with a pyrimidine of the formula VI

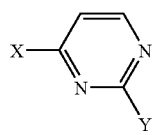

(VI)

in which X is as defined in formula V and

Y is 1) halogen,
2) —O—SO$_2$—R2, or
3) —O—C(O)—R2 to give a compound of the formula VII

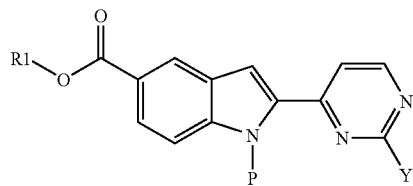

(VII)

in which R1 and P are each as defined in formula IV and Y is as defined in the compound of the formula VI, and then reacting the compound of the formula VII with an amine of the formula VIII

(VIII)

in which R2 and R3 are each as defined in formula I to give a compound of the formula I and detaching any nitrogen protecting group present, or c) reacting the alkyne of the formula IX

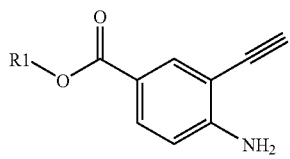

(IX)

in which R1 is as defined in formula I with a pyrimidine of the formula (V) to give an alkyne of the formula X

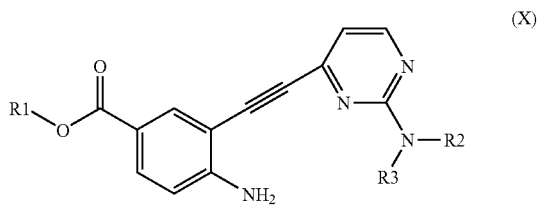

(X)

in which R1, R2 and R3 are each as defined in formula I, and converting the compound of the formula X to the compound of the formula I by ring closure, or d) either isolating the compound of the formula I prepared by processes a), b) or c) in free form or, in the case of the presence of acidic or basic groups, converting it to physiologically compatible salts.

The invention further relates to a process for obtaining the compound of the formula I where R1 is 1) a hydrogen atom,
2) —(C$_1$-C$_6$)-alkyl,
3) phenyl or
4) —(C$_3$-C$_6$)-cycloalkyl, R2 and R3 are the same or different and are each independently a hydrogen atom or
—(C$_1$-C$_4$)-alkyl, wherein a boronoindole of the formula IV
in which R1 is as defined for formula I,
R4 and R5 are the same or different and are each independently —OH or —(C$_1$-C$_6$)-alkyl, or
R4 and R5, together with the boron atom to which they are bonded, form a ring from the group of borolane, borinane, borepane, borocane, [1,3,2]dioxaborolane, [1,3,2]dioxaborinane, [1,3,2]dioxaborepane, [1,3,2]dioxaborocane or [1,3,6,2]dioxazaborocane, P is 1) a hydrogen atom,
2) —C(O)—O—R6 in which R6 is
  a) a hydrogen atom,
  b) —(C$_1$-C$_6$)-alkyl,
  c) —(C$_6$-C$_{14}$)-aryl where aryl is selected from the group of phenyl, naphthyl, anthryl and fluorenyl, and in which aryl is unsubstituted or mono-, di- or trisubstituted by —(C$_1$-C$_6$)-alkyl,
  d) —(C$_3$-C$_6$)-cycloalkyl or
  e) a radical from the group of acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyi, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl, 3) $SO_3$—R6,
4) —O—$SO_2$—R6,
5) —Si—R6 or
6) benzyl is reacted with an aminopyrimidine of the formula V
in which R2 and R3 are the same or different and are each independently a hydrogen atom or —($C_1$-$C_4$)-alkyl, and
X is Cl, Br, I, —O-tosylate, —O-mesylate or —O-acetate, and any nitrogen protecting group present is detached.

The invention further relates to a process for obtaining the compound of the formula I where
R1 is a hydrogen atom or ethyl,
R2 and R3 are the same or different and are each independently a hydrogen atom or —($C_1$-$C_4$)-alkyl, wherein a boronoindole of the formula IV
in which R1 is as defined for formula I,
R4 and R5 are the same and are each —OH, and
P is 1) a hydrogen atom,
2) —O-tosylate or
3) benzyl is reacted with an aminopyrimidine of the formula V
in which R2 and R3 are the same or different and are each independently a hydrogen atom or —($C_1$-$C_4$)-alkyl, and
X is Cl, Br, I, —O-tosylate, —O-mesylate or —O-acetate, and
any nitrogen protecting group present is detached.

The invention further relates to a process for obtaining the compound of the formula I where
R1 is 1) a hydrogen atom,
2) —($C_1$-$C_6$)-alkyl,
3) phenyl or
4) —($C_3$-$C_6$)-cycloalkyl,
R2 and R3 are the same or different and are each independently a hydrogen atom or —($C_1$-$C_4$)-alkyl, wherein a boronoindole of the formula IV
in which R1 is as defined for formula I,
R4 and R5 are the same or different and are each independently —OH or —($C_1$-$C_6$)-alkyl, or R4 and R5, together with the boron atom to which they are bonded, form a ring from the group of borolane, borinane, borepane, borocane, [1,3,2]dioxaborolane, [1,3,2]dioxaborinane, [1,3,2]dioxaborepane, [1,3,2]dioxaborocane or [1,3,6,2]dioxazaborocane,
P is 1) a hydrogen atom,
2) —C(O)—O—R6 in which R6 is
a) a hydrogen atom,
b) —($C_1$-$C_6$)-alkyl,
c) —($C_6$-$C_{14}$)-aryl where aryl is selected from the group of phenyl, naphthyl, anthryl and fluorenyl, and in which aryl is unsubstituted or mono-, di- or trisubstituted by —($C_1$-$C_6$)-alkyl,
d) —($C_3$-$C_6$)-cycloalkyl or
e) a radical from the group of acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyi, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl, 3) $SO_3$—R6,
4) —O—$SO_2$—R6,
5) —Si—R6 or
6) benzyl is reacted with a pyrimidine of the formula VI in which
X is Cl, Br, I, —O-tosylate, —O-mesylate or —O-acetate, and
Y is Cl, Br, I, —O-tosylate, —O-mesylate or O-acetate,
to give a compound of the formula VII and then the compound of the formula VII is reacted with an amine of the formula VIII in which R2 and R3 are the same or different and are each independently a hydrogen atom or —(C$_1$-C$_4$)-alkyl to give a compound of the formula I and any nitrogen protecting group present is detached.

The invention further relates to a process for obtaining the compound of the formula I where R1 is a hydrogen atom or ethyl, R2 and R3 are the same or different and are each independently a hydrogen atom or —(C$_1$-C$_4$)-alkyl, wherein a boronoindole of the formula IV in which R1 is as defined for formula I, R4 and R5 are the same and are each —OH, and P is 1) a hydrogen atom, 2) —O-tosylate or 3) benzyl, is reacted with a pyrimidine of the formula VI in which X is Cl, Br, I, —O-tosylate, —O-mesylate or —O-acetate, and Y is Cl, Br, I, —O-tosylate, —O-mesylate or O-acetate, to give a compound of the formula VII and then the compound of the formula VII is reacted with an amine of the formula VIII in which R2 and R3 are the same or different and are each independently a hydrogen atom or —(C$_1$-C$_4$)-alkyl to give a compound of the formula I and any nitrogen protecting group present is detached.

Process step a) is performed, for example, under the reaction conditions as described by B. Jiang and C. Yang in Heterocycles, Vol. 53, 2000, p. 1489-1498.

The reaction of the boronoindoles (IV) with the pyrimidine derivatives (V) is preferably performed in the presence of catalytic amounts of palladium or nickel compounds such as Pd(PPh$_3$)$_4$, Pd$_2$(dba)$_3$, Pd(OAc)$_2$ or PdCl$_2$/TPPTS.

The reaction temperature is from 40° to 80° C., preferably from 60° C. to 70° C. The reaction time is generally from 2 to 3 hours according to the composition of the mixture and the selected temperature range. Suitable solvents are, for example, methanol, ethanol or toluene. The molar ratio of the compound of the formula IV to the compound of the formula V is, for example, from 1:1 to 1:1.3.

The purity is determined by HPLC.

The compounds of the formula IV are either known or can be prepared, for example, by reacting the corresponding N-protected indole-5-carboxylic acid derivatives (XI) with bases such as LDA, LiTMP or LiHMDS, and subsequent reaction with boric esters such as triisopropyl borate or trimethyl borate (scheme 5).

-Scheme 5-

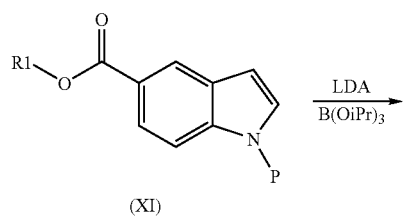

(XI)

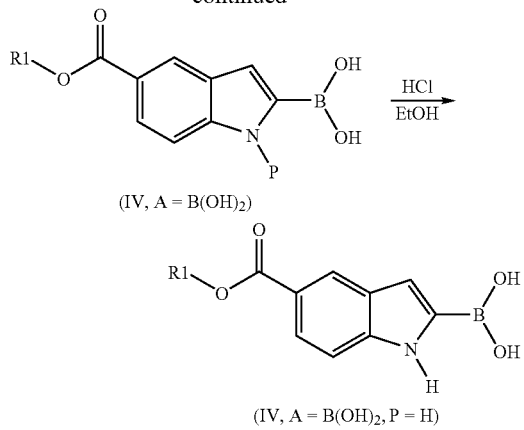

It has been found to be more advantageous to remove the nitrogen protecting group before the actual reaction, since, in this case, the indole (XI) which forms as a by-product during the coupling as a result of detachment of the borono group is formed to a lower degree, which results in a higher yield.

The compounds of the formula V are either known or can be prepared by reacting pyrimidine derivatives (VI) with amines VIII and subsequent removal from the isomer XII, for example by chromatography or steam distillation (see scheme 6).

-Scheme 6-

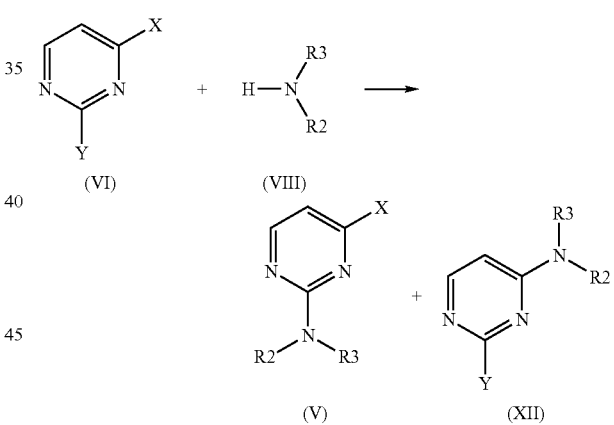

It is also possible to perform the actual reaction with mixtures of (V) and (XII), since it has been found that, surprisingly, the isomer (XII), under the reaction conditions of this coupling, does not react to give (XIII), which is an isomer of (I) (scheme 7)

-Scheme 7-

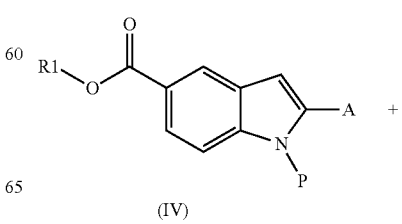

(IV)

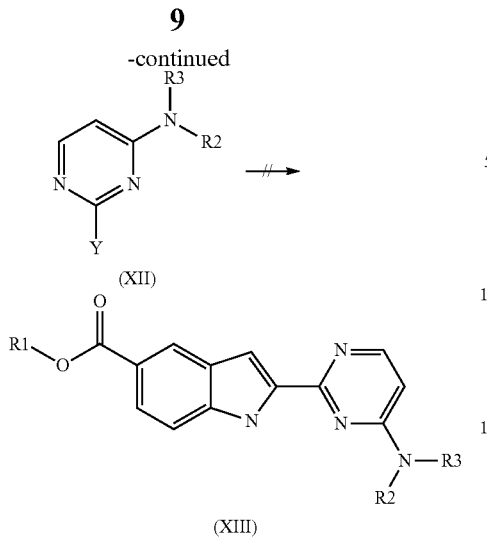

Process step b) is performed analogously to a).

Process step c) is performed, for example, under the reaction conditions as described by 1. Beletskaya et al. in Tetrahedron Letters 44 (2003) 501-5013. The reaction of the compounds of the formula IX with the pyrimidine derivatives (V) is effected preferably in the presence of metal catalysts such as $Pd(OAc)_2$ or CuI and triphenylphosphine or TPPTS. The ring closure of (X) to (I) can be effect, for example, by addition of bases such as KOtBu or KHMDS.

The reaction temperature is from 15° C. to 30° C., preferably from 20° C. to 25° C. The reaction time is generally from 20 to 24 hours according to the composition of the reaction mixture and the selected temperature range. Suitable solvents are, for example, N-methylpyrrolidone (NMP) or dimethylformamide (DMF).

The purity is determined by high-pressure liquid chromatography (HPLC).

The preparation of physiologically compatible salts from compounds of the formula I capable of salt formation, including their stereoisomeric forms, according to process step d) is effected in a manner known per se. The compounds of the formula I form stable alkali metal salts, alkaline earth metal salts or optionally substituted ammonium salts with basic reagents such as hydroxides, carbonates, hydrogencarbonates, alkoxides and ammonia, or organic bases, for example trimethyl- or triethylamine, ethanolamine, diethanolamine or triethanolamine, trometamol or else basic amino acids, for instance lysine, ornithine or arginine. When the compounds of the formula I have basic groups, it is also possible to prepare stable acid addition salts with strong acids. Useful acids for this purpose include both inorganic and organic acids, such as hydrochloric acid, hydrobromic acid, sulfuric acid, hemisulfuric acid, phosphoric acid, methanesulfonic acid, benzenesulfonic acid, p-toluenesulfonic acid, 4-bromobenzenesulfonic acid, cyclohexylamidosulfonic acid, trifluoromethyl-sulfonic acid, 2-hydroxyethanesulfonic acid, acetic acid, oxalic acid, tartaric acid, succinic acid, glycerolphosphoric acid, lactic acid, malic acid, adipic acid, citric acid, fumaric acid, maleic acid, gluconic acid, glucuronic acid, palmitic acid or trifluoroacetic acid.

Preference is given to alkali metals and alkaline earth metals or ammonium salts. Examples of alkali metals and alkaline earth metals are Li, Na, K, Rb, Cs, Be, Mg, Ca, Sr or Ba. An example of an ammonium salt is $NH_4$.

The invention further relates to a process for obtaining the compound of the formula I, wherein a) an aminobenzoic acid of the formula XIV

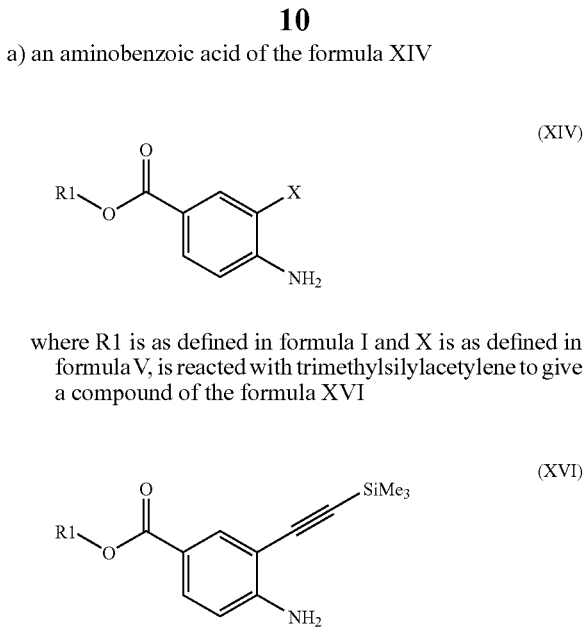

where R1 is as defined in formula I and X is as defined in formula V, is reacted with trimethylsilylacetylene to give a compound of the formula XVI where R1 is as defined in formula I and Me is methyl, and
b) the compound of the formula XVI is converted to an alkyne of the formula IX where R1 is as defined in formula I, and
c) the alkyne of the formula IX is reacted with a pyrimidine of the formula (V) to give an alkyne of the formula X in which R1, R2 and R3 are each as defined in formula I, and the compound of the formula X is converted to the compound of the formula I by ring closure.

The compounds of the formula IX are either known or can be prepared by reacting aminobenzoic acid derivatives (XIV) with trimethylsilylacetylene (XV) and subsequently detaching the silyl protecting group (scheme 8)

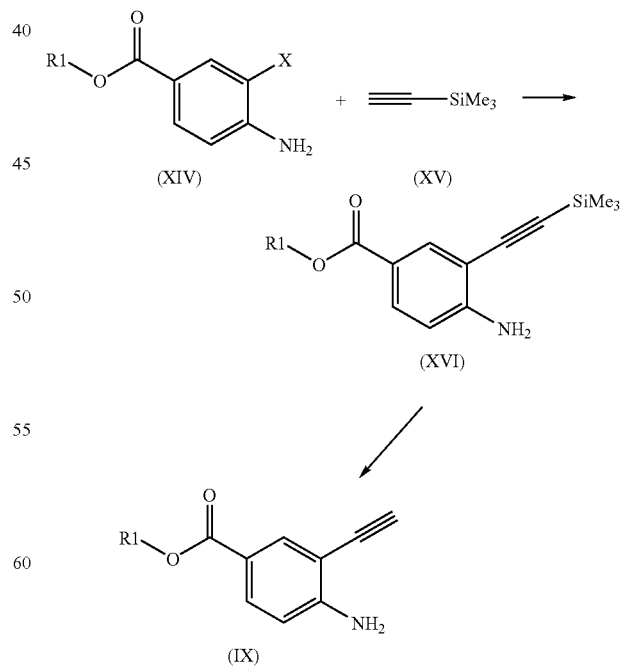

The term "nitrogen protecting group" is understood to mean amine protecting groups customary for P, as described in T. Greene, "Protective Groups in Organic Synthesis". Further examples of nitrogen protecting groups are the radicals 2) to 6) for P as the radical in the compound of the formula II.

The term "catalytic amounts of palladium or nickel compounds" is understood to mean from 0.03 to 0.3 mol (for example based on moles of the compound of the formula IV) of the following compounds $Pd(PPh_3)_4$, $Pd_2(dba)_3$, $Pd(OAc)_2$ or $PdCl_2/TPPTS$.

The term "metal catalysts" is understood to mean, for example, from 0.03 to 0.3 mol (for example based on moles of the compound of the formula IV) of the following compounds $Pd(PPh_3)_4$, $Pd_2(dba)_3$, $Pd(OAc)_2$ or $PdCl_2/TPPTS$.

The terms "—$(C_1$-$C_{12})$-alkyl" are understood to mean hydrocarbon radicals whose carbon chain is straight or branched and contains from 1 to 12 carbon atoms. Examples are methyl, ethyl, propyl, isopropyl, butyl, isobutyl, tert-butyl, pentyl, neopentyl, hexyl, 2,3-dimethylbutane, neohexyl, heptyl, octyl, nonanyl, decanyl or dodecanyl.

The term "$(C_3$-$C_8)$-cycloalkyl" is understood to mean radicals such as compounds which derive from 3- to 8-membered monocycles such as cyclopropyl, cyclobutyl, cyclopentyl, cyclohexyl, cycloheptyl or cyclooctyl.

The terms "—$(C_6$-$C_{14})$-aryl" or "aryl" are understood to mean aromatic carbon radicals having from 6 to 14 carbon atoms in the ring. —$(C_6$-$C_{14})$-Aryl radicals are, for example, phenyl, naphthyl, for example 1-naphthyl, 2-naphthyl, anthryl or fluorenyl.

Naphthyl radicals and especially phenyl radicals are preferred aryl radicals. The term "4- to 15-membered Het ring" are understood to mean ring systems which have from 4 to 15 carbon atoms, are present in one, two or three ring systems bonded to one another and contain one, two, three or four identical or different heteroatoms from the group of oxygen, nitrogen and sulfur. Examples of these ring systems are the acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, benzoimidazolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl radicals.

The term "R4 and R5, together with the boron atom to which they are bonded, form a ring having 4, 5, 6 or 7 carbon atoms in the ring and the ring may, instead of the particular carbon atoms, contain two oxygen atoms or two oxygen atoms and one nitrogen atom" is understood to mean ring systems which derive, for example, from borolane, borinane, borepane, borocane, [1,3,2]dioxaborolane, [1,3,2]dioxaborinane, [1,3,2]-dioxaborepane, [1,3,2]dioxaborocane or [1,3,6,2]dioxazaborocane.

The invention further relates to novel compounds of the formula II

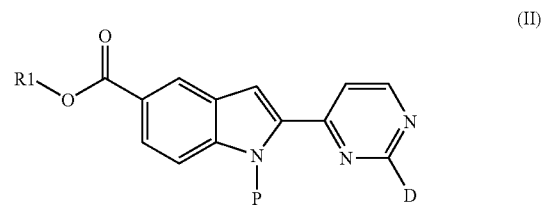

(II)

or a physiologically compatible salt of the compound of the formula II, where

R1 is 1) a hydrogen atom,
2) —$(C_1$-$C_{12})$-alkyl,
3) —$(C_6$-$C_{14})$-aryl,
4) —$(C_3$-$C_8)$-cycloalkyl or
5) a 4- to 15-membered Het ring,
with the proviso that R1 is not a hydrogen atom when P is a hydrogen atom, and D is —N(R2)-R3 in which R2 is a hydrogen atom and R3 is —$(C_1$-$C_4)$-alkyl,
P is 1) a hydrogen atom,
2) —C(O)—O—R6 in which R6 is
a) a hydrogen atom,
b) —$(C_1$-$C_{12})$-alkyl,
c) —$(C_{6-14})$-aryl where aryl is unsubstituted or mono-, di- or tri-substituted by —$(C_1$-$C_6)$-alkyl,
d) —$(C_3$-$C_8)$-cycloalkyl or
e) a 4- to 15-membered Het ring,
3) —$SO_3$—$R_6$,
4) —O—$SO_2$—$R_6$,
5) —Si—$R_6$ or
6) benzyl,
D is 1) —N(R2)-R3,
2) halogen
3) —O—$SO_2$—R2 or
4) —O—C(O)—R2,
in which R2 and R3 are the same or different and are each independently
a) a hydrogen atom,
b) —$(C_1$-$C_{12})$-alkyl,
c) —$(C_{6-14})$-aryl where aryl is unsubstituted or mono-, di- or trisubstituted by —$(C_1$-$C_6)$-alkyl,
d) —$(C_3$-$C_6)$-cycloalkyl or
e) a 4- to 15-membered Het ring.
A further aspect of the invention relates to novel compounds of the formula II in which
R1 is 1) a hydrogen atom,
2) —$(C_1$-$C_6)$-alkyl,
3) phenyl or
4) —$(C_3$-$C_6)$-cycloalkyl,
with the proviso that R1 is not a hydrogen atom when P is a hydrogen atom and D is —N(R2)-R3 in which R2 is a hydrogen atom and R3 is —$(C_1$-$C_4)$-alkyl, D is chlorine, bromine, iodine, fluorine or —N(R2)-R3 where R2 and R3 are the same or different and are each independently a hydrogen atom or —(C$_1$-C$_4$)-alkyl, P is 1) a hydrogen atom,
2) —C(O)—O—R6 in which R6 is
   a) a hydrogen atom,
   b) —(C$_1$-C$_6$)-alkyl,
   c) —(C$_6$-C$_{14}$)-aryl where aryl is selected from the group of phenyl, naphthyl, anthryl and fluorenyl, and in which aryl is unsubstituted or mono-, di- or trisubstituted by —(C$_1$-C$_6$)-alkyl,
   d) —(C$_3$-C$_6$)-cycloalkyl or
   e) a radical from the group of acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, benzimidazolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl,
3) —SO$_3$—R6,
4) —O—SO$_2$—R6,
5) —Si—R6 or
6) benzyl.

A further aspect of the invention relates to novel compounds of the formula II in which
R1 is a hydrogen atom or ethyl,
with the proviso that R1 is not a hydrogen atom when P is a hydrogen atom and D is —N(R2)-R3 in which R2 is a hydrogen atom and R3 is —(C$_1$-C$_4$)-alkyl,
D is chlorine or —N(R2)-R3 where
R2 and R3 are the same or different and are each independently a hydrogen atom or —(C$_1$-C$_4$)-alkyl,
P is a hydrogen atom, —O-tosylate or benzyl.

The compounds of the formula II are obtainable, for example, by process variants a), c) or d) for preparing the compound of the formula I, or arise as intermediates of the formula VII in process variant b) for preparing the compound of the formula I.

The invention further relates to novel compounds of the formula IV

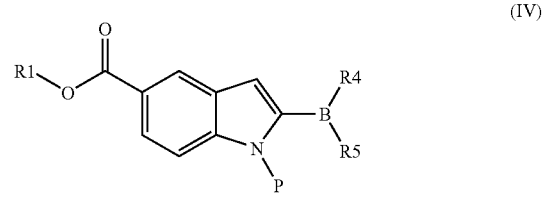

(IV)

where
R1 is 1) a hydrogen atom,
2) —(C$_1$-C$_{12}$)-alkyl,
3) —(C$_6$-C$_{14}$)-aryl,
4) —(C$_3$-C$_8$)-cycloalkyl or
5) a 4- to 15-membered Het ring,
R4 and R5 are the same or different and are each independently
1) —OH,
2) —O—(C$_{1-12}$)-alkyl,
3) —O—(C$_6$-C$_{14}$)-aryl,
4) —O—(C$_3$-C$_8$)-cycloalkyl,
5) —(C$_1$-C$_{12}$)-alkyl or
6) —O-Het,
R4 and R5, together with the boron atom to which they are bonded, form a ring having 4, 5, 6 or 7 carbon atoms in the ring and the ring may, instead of the particular carbon atoms, contain two oxygen atoms or two oxygen atoms and one nitrogen atom,
P is 1) a hydrogen atom,
2) —C(O)—O—R6, in which R6 is
   a) a hydrogen atom,
   b) —(C$_1$-C$_{12}$)-alkyl,
   c) —(C$_{6-14}$)-aryl where aryl is unsubstituted or mono-, di- or tri-substituted by —(C$_1$-C$_6$)-alkyl,
   d) —(C$_3$-C$_8$)-cycloalkyl or
   e) a 4- to 15-membered Het ring,
3) —SO$_3$—R6,
4) —O—SO$_2$—R6,
5) —Si—R6 or
6) benzyl,
with the proviso that R4 and R5 are not —OH or —O—(C$_1$-C$_{12}$)-alkyl, when P is —C(O)—O—(C$_1$-C$_{12}$)-alkyl or R1 is —(C$_1$-C$_{12}$)-alkyl.

The invention further relates to novel compounds of the formula IV where
R1 is 1) a hydrogen atom,
2) —(C$_1$-C$_8$)-alkyl,
3) —(C$_6$-C$_{14}$)-aryl where aryl is selected from the group of phenyl, naphthyl, anthryl and fluorenyl,
4) —(C$_3$-C$_6$)-cycloalkyl or
5) a 4- to 15-membered Het ring, in which Het is a radical from the group of acridinyl, azepinyl, azetidinyl, aziridinyl, benzimidazalinyl, benzimidazolyl, benzofuranyl, benzothiouranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1, 5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl, R4 and R5 are the same or different and are each independently
1) —OH,
2) —O—$(C_1$-$C_{12})$-alkyl,
3) —O—$(C_6$-$C_{14})$-aryl, where aryl is as defined above,
4) —O—$(C_3$-$C_6)$-cycloalkyl,
5) —$(C_{1-6})$-alkyl or
6) —O-Het, where Het is a 4- to 15-membered Het ring and is as defined above, or R4 and R5, together with the boron atom to which they are bonded, form a ring from the group of borolane, borinane, borepane, borocane, [1,3,2]dioxaborolane, [1,3,2]dioxaborinane, [1,3,2]dioxaborepane, [1,3,2]dioxaborocane or [1,3,6,2]dioxazaborocane, and P is a hydrogen atom.

The invention further relates to novel compounds of the formula X

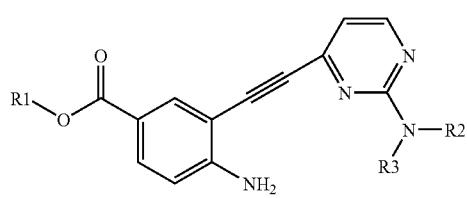

where
R1 is 1) a hydrogen atom,
2) —$(C_1$-$C_{12})$-alkyl,
3) —$(C_6$-$C_{14})$-aryl,
4) —$(C_3$-$C_8)$-cycloalkyl or
5) a 4- to 15-membered Het ring, R2 and R3 are the same or different and are each independently
1) a hydrogen atom,
2) $(C_1$-$C_{12})$-alkyl,
3) —$(C_6$-$C_{14})$-aryl where aryl is unsubstituted or mono-, di- or trisubstituted by —$(C_{1-6})$-alkyl,
4) —$(C_3$-$C_8)$-cycloalkyl or
5) a 4- to 15-membered Het ring.

The compounds of the formula X are obtainable, for example, through process variant c) for preparing the compound of the formula I.

The invention further relates to novel compounds of the formula XVI

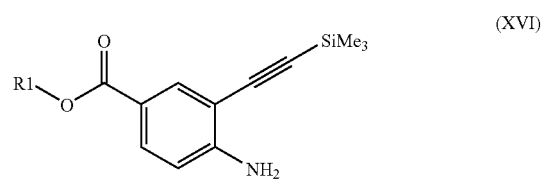

where
R1 is 1) a hydrogen atom,
2) —$(C_1$-$C_{12})$-alkyl,
3) —$(C_6$-$C_{14})$-aryl,
4) —$(C_3$-$C_8)$-cycloalkyl or
5) a 4- to 15-membered Het ring.

The compounds of the formulae II, IV, X, XI or XVI are suitable as intermediates for preparing IkB kinase inhibitors, as described, for example, in WO 01/30774 A1.

The invention is illustrated in detail hereinafter with reference to examples. End products are determined generally by $^1$H NMR (400 MHz, in DMSO-D6). Temperatures are in degrees Celsius; RT means room temperature (22° C. to 26° C.). Abbreviations used are either explained or correspond to the customary conventions.

LIST OF ABBREVIATIONS

Dba dibenzylideneacetone
KHMDS potassium hexamethyldisilazide
KOtBu potassium tert-butoxide
LDA lithium diisopropylamide
LiHMDS lithium hexamethyldisilazide
LiTMP lithium tetramethylpiperazide
OTos

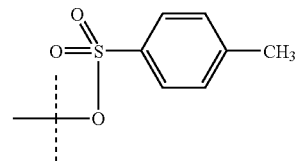

corresponds to —O-tosylate
OMes

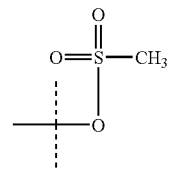

corresponds to —O-mesylate
OAc

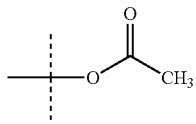

corresponds to —O-acetate
Pd(PPh₃)₄ tetrakis(triphenylphosphine)palladium(0)
Tos

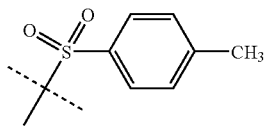

corresponds to tosylate
TPPTS triphenylphosphine trisulfonate
THF tetrahydrofuran Example 1

Synthesis of ethyl 2-(2-chloropyrimidin-4-yl)-1H-indole-5-carboxylate

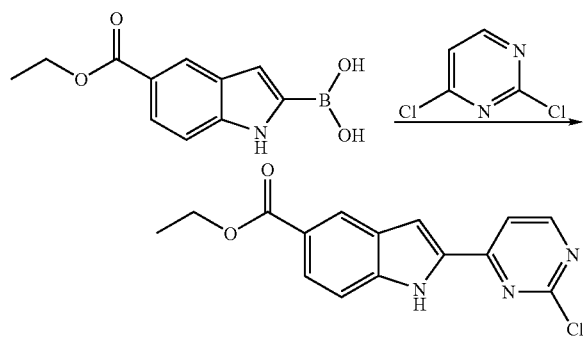

28 g (114 mmol) of 2-borono-5-ethoxycarbonylindole, 12 g (113 mmol) of sodium carbonate and 17.2 g of 2,4-(113 mmol) dichloropyrimidine were initially charged in 412 ml of ethanol. The clear solution was freed of oxygen by vigorous stirring and passing argon through (20 minutes). At RT, 2.67 g of tetrakis(triphenylphosphine)palladium(0) were added. The mixture was heated to from 65° C. to 70° C. for 2 hours (h). Subsequently, 112 ml of water and 112 ml of 30% hydrochloric acid were added and the mixture was cooled to 0° C. After filtration and drying under reduced pressure, 37.3 g (93% of theory) of ethyl 2-(2-chloropyrimidin-4-yl)-1H-indole-5-carboxylate were obtained (HPLC>96%).

The purity was determined by high-pressure liquid chromatography (HPLC):

| Column: | Waters Symetry Shield RP8 3.9 * 150 | | |
|---|---|---|---|
| Temperature: | 40° C. | | |
| Flow rate: | 1 ml/min | Injection volume: | 10 µl |
| Pressure: | 90 bar | UV: | 254 nm |

-continued

| Eluent: | A: Water/trifluoroacetic acid (0.05%) | | | | |
|---|---|---|---|---|---|
| | B: Acetonitrile/trifluoroacetic acid (0.05%) | | | | |
| Time (min) | 0 | 15 | 20 | 25 | 30 |
| A (%) | 80 | 25 | 25 | 80 | 80 |
| B (%) | 20 | 75 | 75 | 20 | 20 |
| Retention time of title compound: 12.6 min | | | | | |

Example 2

Synthesis of ethyl 2-(2-methylaminopyrimidin-4-yl)-1H-indole-5-carboxylate

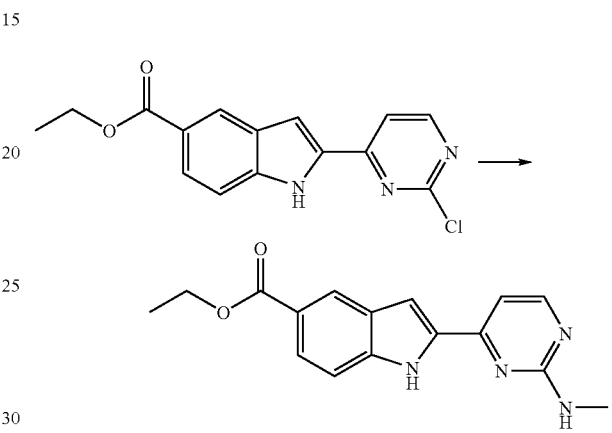

30 g (95.4 mmol) of ethyl 2-(2-chloropyrimidin-4-yl)-1H-indole-5-carboxylate were initially charged and suspended in 150 ml of ethanol. 53.9 g of methylamine solution in ethanol (8 M) were added to this suspension which was heated to from 75° C. to 80° C. in an autoclave for 4 h. After concentration and washing with ethanol, 29.7 g of ethyl 2-(2-methylaminopyrimidin-4-yl)-1H-indole-5-carboxylate were obtained (97.6 HPLC area %).

LCMS: [M+H]⊕297.12

HPLC method as in example 1; retention time of title compound: 5.8 min

Example 3

Synthesis of 2-(2-methylaminopyrimidin-4-yl)-1H-indole-5-carboxylic acid sodium salt

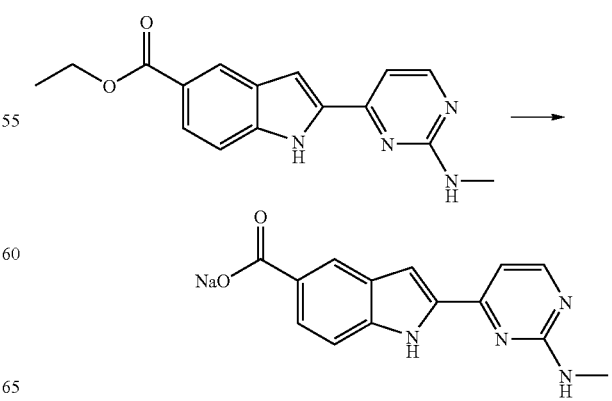

25 g of ethyl 2-(2-methylaminopyrimidin-4-yl)-1H-indole-5-carboxylate were admixed with 200 ml of ethanol and 24.5 g of 33% sodium hydroxide solution, and heated to from 65° C. to 70° C. for 4 h. After cooling, the mixture was filtered with suction and the precipitate was washed with 15 ml of ethanol/water (9:1). 24.5 g (87.6% of theory) of 2-(2-methylaminopyrimidin-4-yl)-1H-indole-5-carboxylic acid sodium salt were obtained (98.1 HPLC area %). LCMS: [M+H] ⊕269.10

HPLC method as in example 1; retention time of title compound: 3.3 min

Example 4

Synthesis of methyl 4-amino-3-trimethylsilylethynylbenzoate

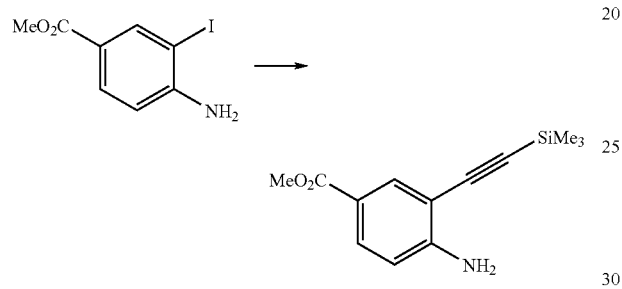

5.83 g (20 mmol) of methyl 4-aminobenzoate, 20.2 g (198 mmol) of triethylamine and 80 ml of toluene were initially charged. The clear solution was freed of oxygen by vigorous stirring and passing argon through (20 minutes). At an internal temperature of 20° C., 3.2 g (33 mmol) of trimethylsilylacetylene, 76 mg of copper(I) iodide and 52 mg of triphenylphosphine were added. After aqueous workup, 5.45 g of 4-amino-3-trimethylsilylethynylbenzoate were obtained (HPLC: >99 area %). HPLC method as in example 1.

Example 5

Synthesis of methyl 4-amino-3-ethynylbenzoate

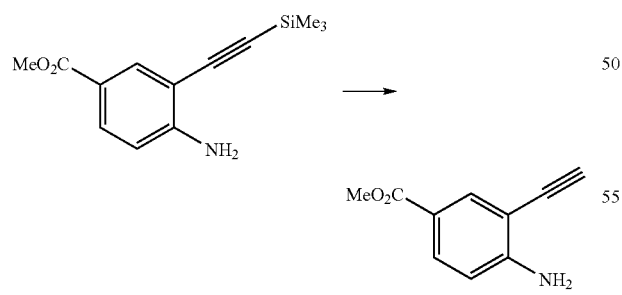

1.9 g (7.7 mmol) of methyl 4-amino-3-trimethylsilylethynylbenzoate were initially charged in 20 ml of tetrahydrofuran (THF). At from 5° C. to 8° C., 8.45 ml (8.5 mmol) of tetrabutylammonium fluoride solution (1 M in THF) were added dropwise within 5 minutes. After 25 mm at 2° C., 438 ml of acetic acid were added. After addition of water and extraction with dichloromethane, and after removal of the solvent, 1.35 g of methyl 4-amino-3-ethynylbenzoate were obtained. HPLC method as in example 1.

Example 6

Synthesis of methyl 4-amino-3-(1-methylaminopyrimidin-4-yl)-ethynylbenzoate

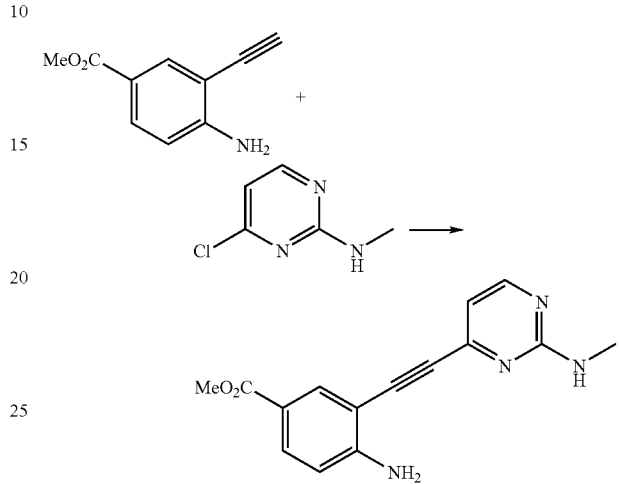

3.0 g (17 mmol) of methyl 4-amino-3-ethynylbenzoate and 2.6 g (19 mmol) of 4-chloro-2-methylaminopyrimidine were initially charged in 20 ml of dimethylformamide (DMF) and 8.7 g (85 mmol) of triethylamine, and degassed with argon while stirring for 5 min. Subsequently, 65 mg of copper(I) iodide and 20 mg of tetrakis(triphenylamine)palladium(0) were added and the mixture was heated to 71° C. for 3 h. After aqueous workup, 4.1 g of methyl 4-amino-3-(1-methylaminopyrimidin-4-yl)ethynylbenzoate were obtained. (HPLC: 99.7 area %) HPLC method as in example 1.

Example 7

Synthesis of methyl 2-(2-methylaminopyrimidin-4-yl)-1H-indole-5-carboxylate by cyclizing methyl 4-amino-3-(1-methylaminopyrimidin-4-yl)ethynyl benzoate

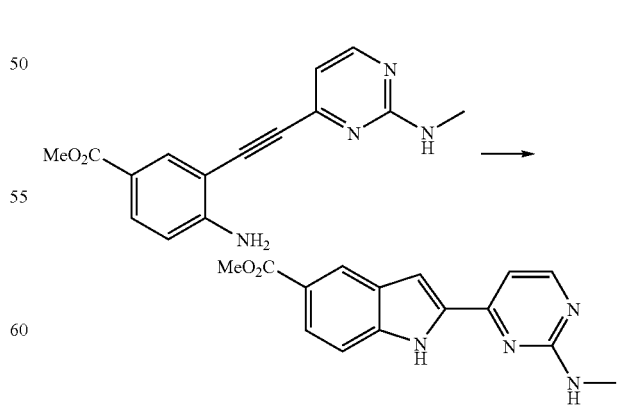

73 mg (0.7 mmol) of potassium tert-butoxide were dissolved in 1 ml of NMP and admixed with a solution of 140 mg (0.5 mmol) of methyl 4-amino-3-(1-methylaminopyrimidin- 4-yl)ethynylbenzoate in 1 ml of NMP. Subsequently, stirring was continued at RT for 24 h. Aqueous workup afforded 115 mg of methyl 2-(2-methylaminopyrimidin-4-yl)-1H-indole-5-carboxylate (HPLC: 92.3 area %).

Example 8

Synthesis of 2-borono-5-ethoxycarbonylindole

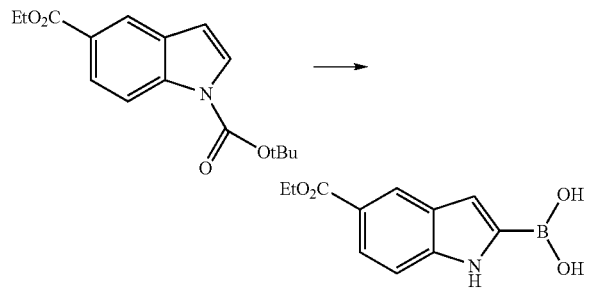

150 g (519 mmol) of N-Boc-5-ethoxycarbonylindole and 192 ml (833 mmol) of triisopropyl borate in 350 ml of toluene were admixed at from 5° C. to 10° C. with 350 ml of a 1.8 molar solution of LDA in THF. The mixture was stirred for a further 5 min and the reaction mixture was added to a solution of 278 g of 30% hydrochloric acid and 940 ml of water. Subsequently, the mixture was stirred at from 5° C. to 10° C. for 30 min. Thereafter, the mixture was filtered and the filtercake was suspended in 530 ml of ethanol. This suspension was added at 40° C. to a solution of 500 ml of 30% hydrochloric acid and 224 ml of ethanol. Subsequently, the mixture was stirred at from 40° C. to 45° C. for 2.5 h and admixed at 30° C. with 380 ml of water. The mixture was then cooled to from 10° C. to 15° C., stirred at this temperature for 30 min and filtered. Drying under reduced pressure afforded 79.5 g (61% of theory) of 2-borono-5-ethoxycarbonylindole (HPLC: 92.7 area %).

What is claimed is:

1. A process for obtaining a compound of formula Ia:

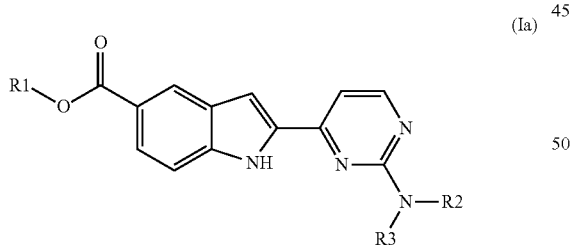

where
R1 is a hydrogen atom,
—($C_1$-$C_{12}$)-alkyl,
—($C_6$-$C_{14}$)-aryl,
—($C_3$-$C_8$)-cycloalkyl or
a 4- to 15-membered Het ring,
R2 and R3 are the same or different and are each independently
a hydrogen atom,
($C_1$-$C_{12}$)-alkyl,
—($C_6$-$C_{14}$)-aryl where aryl is unsubstituted or mono-, di- or trisubstituted by —($C_{1-6}$)-alkyl,
—($C_3$-$C_8$)-cycloalkyl or
a 4- to 15-membered Het ring,
said process comprising the steps of:
a) reacting a boronoindole of the formula IV

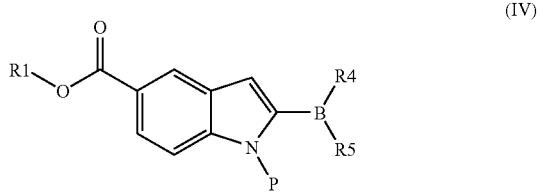

in which R1 is as defined in formula Ia,
R4 and R5 are the same or different and are each independently
—OH,
—O—($C_1$-$C_{12}$)-alkyl,
—O—($C_6$-$C_{14}$)-aryl,
—O—($C_{3-8}$)-cycloalkyl,
—($C_1$-$C_{12}$)-alkyl or
—O-Het, where Het is a 4- to 15-membered Het ring,
or
R4 and R5, together with the boron atom to which they are bonded, form a ring having 4, 5, 6 or 7 carbon atoms in the ring and the ring may, instead of the particular carbon atoms, contain two oxygen atoms or two oxygen atoms and one nitrogen atom,
P is a hydrogen atom or a nitrogen protecting group,
with an aminopyrimidine of the formula V

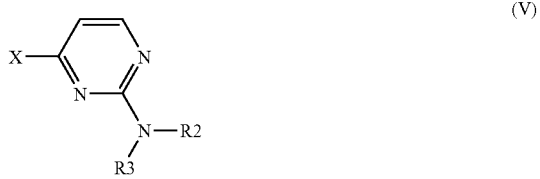

in which R2 and R3 are each as defined in formula Ia and
X is halogen,
—O—$SO_2$—R2, or
—O—C(O)—R2,
and detaching any nitrogen protecting group present, or
b) reacting a boronoindole of the formula IV with a pyrimidine of the formula VI

in which X is as defined in formula V and
Y is halogen,
—O—$SO_2$—R2, or
—O—C(O)—R2 to give a compound of the formula VII

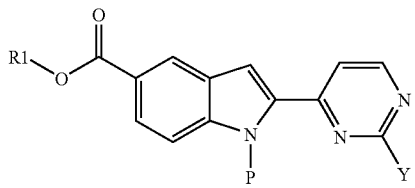

in which R1 and P are each as defined in formula IV and Y is as defined in the compound of the formula VI,
and then reacting the compound of the formula VII with an amine of the formula VIII

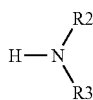

in which R2 and R3 are each as defined in formula Ia
to give a compound of the formula Ia and detaching any nitrogen protecting group present, or
c) reacting the alkyne of the formula IX

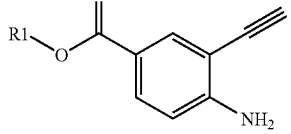

in which R1 is as defined in formula Ia
with a pyrimidine of the formula (V) to give an alkyne of the formula X

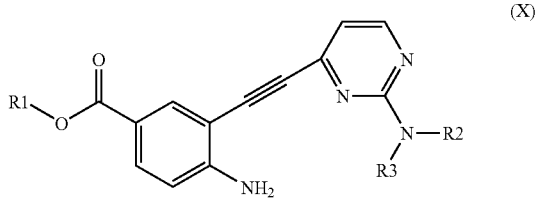

in which R1, R2 and R3 are each as defined in formula Ia, and converting the compound of the formula X to the compound of the formula Ia by ring closure, or
d) either isolating the compound of the formula Ia prepared by processes a), b) or c) in free form or, in the case of the presence of acidic or basic groups, converting it to physiologically compatible salts.

2. The process for obtaining the compound of the formula Ia as claimed in claim 1 where
R1 is a hydrogen atom,
—$(C_1\text{-}C_6)$-alkyl,
phenyl or
—$(C_3\text{-}C_6)$-cycloalkyl,
R2 and R3 are the same or different and are each independently
a hydrogen atom or —$(C_1\text{-}C_4)$-alkyl,
wherein a boronoindole of the formula IV
in which R1 is as defined for formula Ia,
R4 and R5 are the same or different and are each independently —OH or —$(C_1\text{-}C_6)$-alkyl, or
R4 and R5, together with the boron atom to which they are bonded, form a ring from the group of borolane, borinane, borepane, borocane, [1,3,2]dioxaborolane, [1,3,2]dioxaborinane, [1,3,2]dioxaborepane, [1,3,2]dioxaborocane or [1,3,6,2]dioxazaborocane,
P is a hydrogen atom;
—C(O)—O—R6 in which
R6 is
—$(C_1\text{-}C_6)$-alkyl,
—$(C_6\text{-}C_{14})$-aryl where aryl is selected from the group of phenyl, naphthyl, anthryl and fluorenyl, and in which aryl is unsubstituted or mono-, di- or trisubstituted by —$(C_1\text{-}C_6)$-alkyl,
—$(C_3\text{-}C_6)$-cycloalkyl or
a radical from the group of acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran-[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl;
$SO_3$—R6;
—O—$SO_2$—R6;
—Si—R6; or
benzyl;
is reacted with an aminopyrimidine of the formula V
in which R2 and R3 are the same or different and are each independently a hydrogen atom or —$(C_1\text{-}C_4)$-alkyl, and
X is Cl, Br, I, —O-tosylate, —O-mesylate or —O-acetate.

3. The process for obtaining the compound of the formula Ia as claimed in claim 1 where
R1 is a hydrogen atom or ethyl,
R2 and R3 are the same or different and are each independently a hydrogen atom or —$(C_1\text{-}C_4)$-alkyl, wherein a boronoindole of the formula IV
in which R1 is as defined for formula Ia,
R4 and R5 are the same and are each —OH, and
P is a hydrogen atom,
—O-tosylate or
benzyl
is reacted with an aminopyrimidine of the formula V
in which R2 and R3 are the same or different and are each independently a hydrogen atom or —($C_1$-$C_4$)-alkyl, and
X is Cl, Br, I, —O-tosylate, —O-mesylate or —O-acetate.

4. The process of claim 1, wherein the reaction of the boronoindoles of the formula IV with the pyrimidine derivatives of the formula V is performed in the presence of catalytic amounts of palladium or nickel compounds.

5. The process as claimed in claim 4, wherein the reaction temperature is from 40° C. to 80° C.

6. The process as claimed in claim 4, wherein the molar ratio of the compound of the formula IV to the compound of the formula V is from 1:1 to 1:1.3.

7. The process for obtaining the compound of the formula Ia as claimed in claim 1 where
R1 is a hydrogen atom,
—($C_1$-$C_6$)-alkyl,
phenyl or
—($C_3$-$C_6$)-cycloalkyl,
R2 and R3 are the same or different and are each independently
a hydrogen atom or —($C_1$-$C_4$)-alkyl,
wherein a boronoindole of the formula IV
in which R1 is as defined for formula Ia,
R4 and R5 are the same or different and are each independently
—OH or —($C_1$-$C_6$)-alkyl, or
R4 and R5, together with the boron atom to which they are bonded, form a ring from the group of borolane, borinane, borepane, borocane, [1,3,2]dioxaborolane, [1,3,2]dioxaborinane, [1,3,2]dioxaborepane, [1,3,2]dioxaborocane or [1,3,6,2]dioxazaborocane,
P is a hydrogen atom;
—C(O)—O—R6 in which
R6 is
a hydrogen atom,
—($C_1$-$C_6$)-alkyl,
—($C_6$-$C_{14}$)-aryl where aryl is selected from the group of phenyl, naphthyl, anthryl and fluorenyl, and in which aryl is unsubstituted or mono-, di- or trisubstituted by
—($C_1$-$C_6$)-alkyl,
—($C_3$-$C_6$)-cycloalkyl or
a radical from the group of acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzoisoxazolyl, benzoisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran-[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl or xanthenyl;

$SO_3$—R6;

—O—$SO_2$—R6;

—Si—R6; or benzyl;

is reacted with a pyrimidine of the formula VI in which

X is Cl, Br, I, —O-tosylate, —O-mesylate or —O-acetate, and

Y is Cl, Br, I, —O-tosylate, —O-mesylate or O-acetate, to give a compound of the formula VII and then the compound of the formula VII is reacted with an amine of the formula VIII in which R2 and R3 are the same or different and are each independently a hydrogen atom or —($C_1$-$C_4$)-alkyl to give a compound of the formula Ia.

8. The process for obtaining the compound of the formula Ia as claimed in claim 7 where R1 is a hydrogen atom or ethyl, R2 and R3 are the same or different and are each independently a hydrogen atom or —($C_1$-$C_4$)-alkyl, wherein a boronoindole of the formula IV in which R1 is as defined for formula Ia, R4 and R5 are the same and are each —OH, and P is a hydrogen atom, —O-tosylate or benzyl, is reacted with a pyrimidine of the formula VI in which X is Cl, Br, I, —O-tosylate, —O-mesylate or —O-acetate, and Y is Cl, Br, I, —O-tosylate, —O-mesylate or O-acetate, to give a compound of the formula VII and then the compound of the formula VII is reacted with an amine of the formula VIII in which R2 and R3 are the same or different and are each independently a hydrogen atom or —($C_1$-$C_4$)-alkyl to give a compound of the formula Ia and any nitrogen protecting group present is detached.

9. The process as claimed in claim 1, wherein the reaction of the alkyne of the formula IX with the pyrimidine of the formula V to give an alkyne of the formula X is performed at a reaction temperature of from 15° C. to 30° C.

10. The process as claimed in claim 9, wherein the reaction is performed in a solvent selected from N-methylpyrrolidone and dimethylformamide.

11. The process as claimed in claim 1, wherein
a) an aminobenzoic acid of the formula XIV

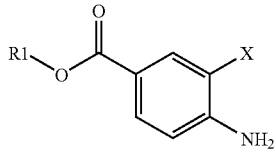
(XIV)

where R1 is as defined in formula Ia and X is as defined in formula V, is reacted with trimethylsilylacetylene to give a compound of the formula XVI

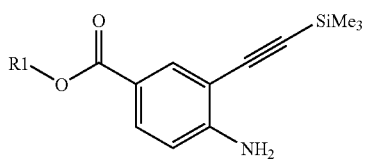
(XVI)

where R1 is as defined in formula Ia and Me is methyl, and
b) the compound of the formula XVI is converted to an alkyne of the formula IX where R1 is as defined in formula Ia, and
c) the alkyne of the formula IX is reacted with a pyrimidine of the formula (V) to give an alkyne of the formula X in which R1, R2 and R3 are each as defined in formula Ia, and the compound of the formula X is converted to the compound of the formula Ia by ring closure.

12. The process of claim 1, wherein the reaction of the boronoindoles of the formula IV with the pyrimidine derivatives of the formula V is performed in the presence of catalytic amounts of palladium compounds.

13. The process of claim 12, wherein said palladium compounds are selected from $Pd(PPh_3)_4$, $Pd_2(dba)_3$, $Pd(OAc)_2$ and $PdCl_2$/TPPTS.

14. The process as claimed in claim 5, wherein said reaction temperature is from 60° C. to 70° C.

15. The process as claimed in claim 1, wherein the reaction of the alkyne of the formula IX with the pyrimidine of the formula V to give an alkyne of the formula X is performed at a reaction temperature of from 20° C. to 25° C.

16. The process as claimed in claim 1, wherein P is a hydrogen atom.

* * * * *

UNITED STATES PATENT AND TRADEMARK OFFICE
CERTIFICATE OF CORRECTION

PATENT NO. : 8,232,395 B2
APPLICATION NO. : 11/949294
DATED : July 31, 2012
INVENTOR(S) : Joachim Graeser et al.

It is certified that error appears in the above-identified patent and that said Letters Patent is hereby corrected as shown below:

On the Title page, in field (56), in column 2, under "Other Publications", line 2, delete "Dihydroindo1" and insert -- Dihydroindol --, therefor.

In column 5, line 13, delete "oxothiolanyl," and insert -- oxathiolanyl, --, therefor.

In column 5, line 17, delete "pyroazolidinyl," and insert -- pyrazolidinyl, --, therefor.

In column 5, line 26, delete "thienooxazolyi," and insert -- thienooxazolyl, --, therefor.

In column 6, line 40, delete "oxothiolanyl," and insert -- oxathiolanyl, --, therefor.

In column 6, line 44, delete "pyroazolidinyl," and insert -- pyrazolidinyl, --, therefor.

In column 6, line 53, delete "thienooxazolyi," and insert -- thienooxazolyl, --, therefor.

In column 11, line 53, delete "oxothiolanyl," and insert -- oxathiolanyl, --, therefor.

In column 11, line 56-57, delete "pyroazolidinyl," and insert -- pyrazolidinyl, --, therefor.

In column 13, line 35, delete "oxothiolanyl," and insert -- oxathiolanyl, --, therefor.

In column 13, line 39, delete "pyroazolidinyl," and insert -- pyrazolidinyl, --, therefor.

In column 15, line 8, delete "oxothiolanyl," and insert -- oxathiolanyl, --, therefor.

In column 15, line 12, delete "pyroazolidinyl," and insert -- pyrazolidinyl, --, therefor.

In column 17, line 63, delete "Symetry" and insert -- Symmetry --, therefor.

Signed and Sealed this
Thirtieth Day of October, 2012

David J. Kappos
*Director of the United States Patent and Trademark Office*

CERTIFICATE OF CORRECTION (continued)
U.S. Pat. No. 8,232,395 B2

In column 24, line 39, in claim 2, delete "oxothiolanyl," and insert -- oxathiolanyl, --, therefor.

In column 24, line 43, in claim 2, delete "pyroazolidinyl," and insert -- pyrazolidinyl, --, therefor.

In column 26, line 1, in claim 7, delete "oxothiolanyl," and insert -- oxathiolanyl, --, therefor.

In column 26, line 5, in claim 7, delete "pyroazolidinyl," and insert -- pyrazolidinyl, --, therefor.